US00PP36703P2

(12) United States Plant Patent
Steffen

(10) Patent No.: US PP36,703 P2
(45) Date of Patent: May 20, 2025

(54) ***ANGELONIA* PLANT NAMED 'ANGAF19202'**

(50) Latin Name: *Angelonia hybrida*
Varietal Denomination: ANGAF19202

(71) Applicant: Elsner pac Vertriebsgesellschaft mbH Berlin, Thiendorf (DE)

(72) Inventor: Elke Steffen, Erfurt (DE)

(73) Assignee: Elsner pac Vertriebsgesellschaft mbH Berlin, Thiendorf (DE)

( * ) Notice: Subject to any disclaimer, the term of this patent is extended or adjusted under 35 U.S.C. 154(b) by 0 days.

(21) Appl. No.: 18/772,976

(22) Filed: Jul. 15, 2024

(51) Int. Cl.
*A01H 5/02* (2018.01)
*A01H 6/68* (2018.01)

(52) U.S. Cl.
USPC ..... Plt./404
CPC ..... *A01H 6/68* (2018.05)

(58) Field of Classification Search
USPC ..... Plt./404
CPC ..... A01H 5/02
See application file for complete search history.

*Primary Examiner* — Kent L Bell
(74) *Attorney, Agent, or Firm* — The Webb Law Firm

(57) ABSTRACT

A new and distinct freely flowering *Angelonia* plant with large, white flowers.

1 Drawing Sheet

Botanical classification: *Angelonia hybrida.*
Varietal denomination: 'ANGAF19202'.

BACKGROUND OF THE INVENTION

The present invention comprises a new and distinct variety of *Angelonia hybrida* known by the varietal name 'ANGAF19202'. The new variety was discovered in August of 2019 in a planned breeding program in Dresden, Germany. The purposes of the breeding program were to develop freely flowering plants that are suitable for containers, bedding, and as cut flowers. The new variety is the result of a cross between an unpatented *Angelonia hybrida* variety having an internal breeder's reference of "AN-17004" (female parent) and pollination from a group of unpatented *Angelonia hybrida* plants from the breeder's own collection. As such, the exact male parent from this collection is unknown. The new variety was first asexually reproduced in January of 2020 by terminal cuttings in Dresden, Germany. The new variety has been trial and field tested in Thiendorf, Germany and has been found to retain its distinctive characteristics and remain true to type through successive propagations.

The new variety is similar to its female parent in having white flowers and long shoots, but has an earlier flowering time than its female parent. The new variety is similar to *Angelonia* variety named 'Ansuwhi' (U.S. Plant Pat. No. 29,490) in having freely flowering, white flowers, but the new variety exhibits more branches with shorter internodes. The following characteristics further distinguish the new variety from other *Angelonia* varieties known to the breeder:

Overall height of plant is tall;
Long and dense inflorescences; and
Large, single flowers.

DESCRIPTION OF THE DRAWING

The accompanying photographic drawing illustrates the new variety at 20 weeks of age, with the color being as nearly true as is possible with color illustrations of this type.

DESCRIPTION OF THE PLANT

The following detailed description sets forth the characteristics of the new cultivar. The data that defines these characteristics were collected by asexual reproductions carried out in a greenhouse in Thiendorf, Germany on plants at 20 weeks of age that were grown in 13.0 cm diameter pots. The color readings were taken on a plant indoors under natural light. Color references are primarily to the 1995 edition of The R.H.S. Colour Chart of The Royal Horticultural Society of London, except where terms of ordinary color significance are used.

PLANT

Form: Broadly upright.
Height (from soil): 40.0-70.0 cm to top of foliage, 60.0-100.0 cm to top of flowers.
Diameter: 30.0 cm.
Growth: Well-branched from the base and vigorous.
Time to initiate roots: About 10-14 days at 20° C.
Time to develop roots: About 21-28 days at 20° C.
Rooting habit: Fine, fibrous, and of medium density.
Disease/pest resistance/susceptibility: Nothing unusual noted to date.
Weather tolerance: Good rain tolerance.
Seed/fruit production: None observed to date.
Main stem:
- *Form.*—Upright and slightly rectangular in cross section.
- *Color.*—Close to 144B.
- *Texture.*—Smooth.
- *Length.*—Approximately 60.0 cm.
- *Diameter.*—2.0-3.0 cm.
- *Internode length.*—0.8-2.5 cm.

Foliage:
- *Arrangement (e.g., alternate, single).*—Opposite, decussate, simple sessile.
- *Number of leaves per branch.*—About 40-60.
- *Size of leaf.*—Length: 5.0-10.0 cm. Width: 1.0-2.5 cm.

*Shape of leaf* (*generally*).—Lanceolate.
*Shape of apex*.—Acute.
*Shape of base*.—Attenuate.
*Texture*.—Smooth and glossy.
*Margin type*.—Serrate.
*Color*.—Young leaves: Upper surface: Close to 146A. Lower surface: Close to 146B. Mature leaves: Upper surface: Close to 147A. Lower surface: Close to 146A.
*Petiole*.—Not present.
*Veins*.—Venation type: Longitudinal. Color: Upper surface: From 144B to 146B. Lower surface: Close to 147A.

FLOWER

Natural flowering season at specified location(s): From spring to autumn in central Europe.
Flower type and habit: Single flowers arranged in upright, terminal racemes.
Number of flowers per plant: From 30-70.
Bud (described shortly before opening):
*Shape*.—Globose.
*Diameter*.—10.0 mm.
*Length*.—8.0 mm.
*Color*.—150D.
Flower:
*Shape*.—Two-lipped corolla with five lobes, with the two upper lobes typically reflexed. There are no single petals.
*Corolla diameter*.—Approximately 30.0 mm.
*Corolla length*.—Approximately 5.0 mm.
*Lobe shape*.—Rounded.
*Texture*.—Smooth.
*Fragrance*.—None detected.
*Lasting quality*.—High.
*Color*.—When opening: Upper surface: 155A to 155D. Lower surface: 155A. Fully opened: Upper surface: 155D. Lower surface: 155D.
Sepal:
*Number*.—5.
*Length*.—5.0 mm.
*Width*.—2.0 mm.
*Shape*.—Lanceolate.
*Apex*.—Acute.
*Base*.—Fused.
*Margin*.—Entire.
*Color*.—143B.
Peduncle: Not present.
Pedicel:
*Length*.—15.0-22.0 mm.
*Diameter*.—1.0 mm.
*Color*.—145A.

REPRODUCTIVE ORGANS

Stamens:
*Number* (*per flower*).—4.
*Filament length*.—3.0 mm.
*Anthers*.—Shape: Elliptic. Length: 1.0-2.0 mm. Color: 158A.
*Pollen*.—Color: 158A. Amount: Moderate.
Pistils:
*Length*.—5.0 mm.
*Style*.—Length: 4.0 mm. Color: 158A.
*Ovaries*.—Length: 1.0-2.0 mm. Color: 145B.
*Stigma*.—Shape: Beaked. Color: 155D.

I claim:

1. A new and distinct variety of *Angelonia* plant named 'ANGAF19202', as is herein illustrated and described.

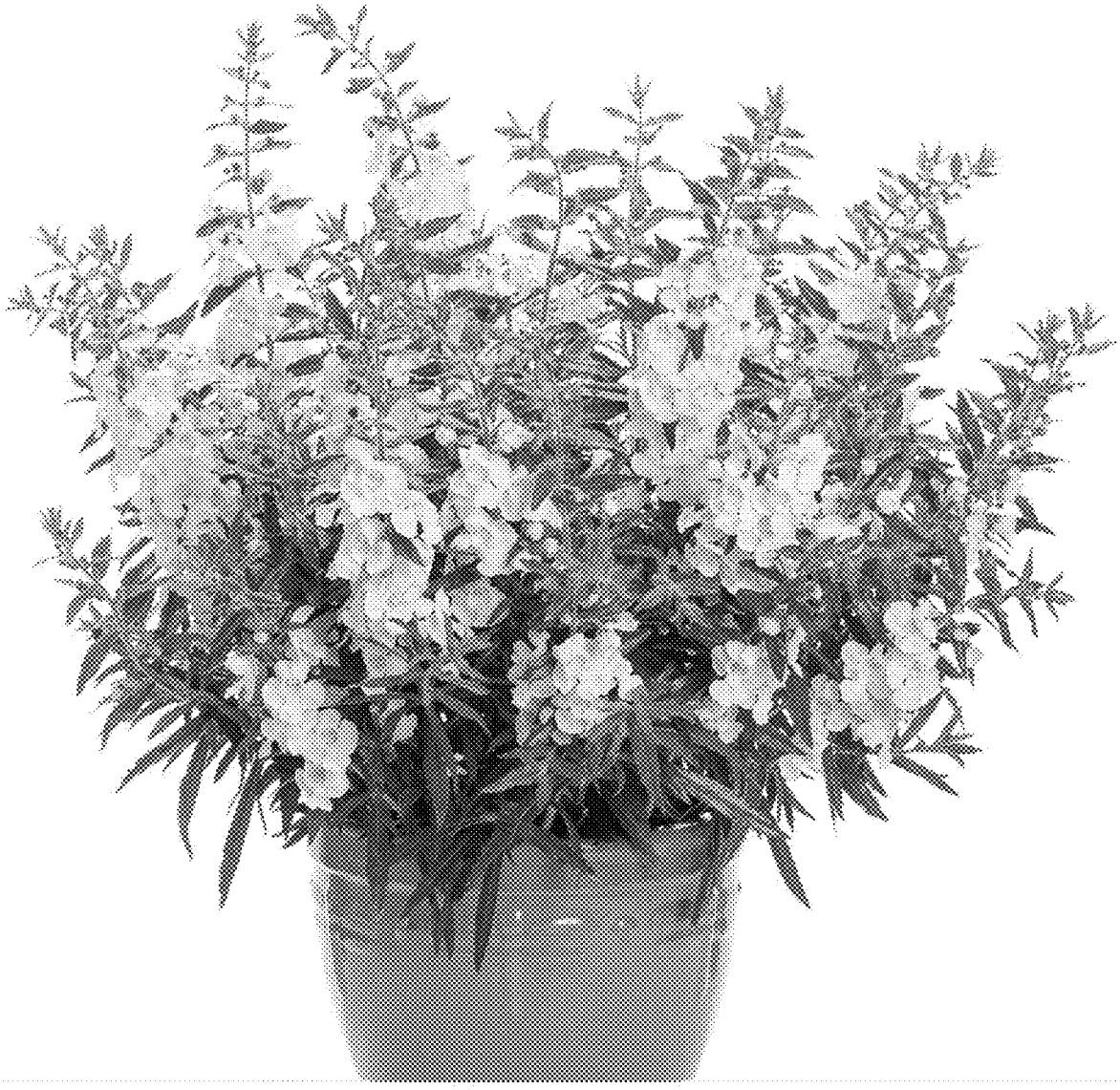

* * * * *